United States Patent [19]

Jenczewski et al.

[11] Patent Number: 5,656,757

[45] Date of Patent: Aug. 12, 1997

[54] MONOMER RECOVERY FROM MULTI-COMPONENT MATERIALS

[75] Inventors: Theodore John Jenczewski, Midlothian; Lamberto Crescentini, Chester; Richard Eugene Mayer, Richmond, all of Va.

[73] Assignee: AlliedSignal Inc., Morristown, N.J.

[21] Appl. No.: 511,334

[22] Filed: Aug. 10, 1995

[51] Int. Cl.$^6$ .............................................. C07D 201/12
[52] U.S. Cl. .................................................. 540/540
[58] Field of Search ..................................... 540/540

[56] References Cited

U.S. PATENT DOCUMENTS

| | | | |
|---|---|---|---|
| 3,182,055 | 5/1965 | Bonfield et al. | 260/239.3 |
| 3,317,519 | 5/1967 | Lazarus et al. | 260/239.3 |
| 3,742,093 | 6/1973 | Skidmore | 260/893 |
| 3,917,507 | 11/1975 | Skidmore | 159/2 E |
| 3,939,153 | 2/1976 | Fowler | 260/239.3 |
| 4,051,212 | 9/1977 | Grigat et al. | 264/102 |
| 4,107,160 | 8/1978 | Dicoi et al. | 260/239.3 |
| 4,136,251 | 1/1979 | Bice et al. | 528/486 |
| 4,311,642 | 1/1982 | Crescentini et al. | 260/239.3 |
| 4,360,461 | 11/1982 | Fuchs et al. | 260/239.3 |
| 4,578,510 | 3/1986 | Doerr | 562/483 |
| 4,605,762 | 8/1986 | Mandoki | 562/483 |
| 4,620,032 | 10/1986 | Doerr | 562/483 |
| 4,683,305 | 7/1987 | Fuchs et al. | 540/533 |
| 4,764,607 | 8/1988 | Balint et al. | 540/540 |
| 5,169,870 | 12/1992 | Corbin et al. | 521/49.8 |
| 5,216,149 | 6/1993 | Evans et al. | 540/538 |
| 5,233,037 | 8/1993 | Nielinger et al. | 540/540 |
| 5,241,066 | 8/1993 | Davis et al. | 540/540 |
| 5,266,694 | 11/1993 | Moran, Jr. | 540/540 |
| 5,294,707 | 3/1994 | Kotek | 540/540 |
| 5,302,756 | 4/1994 | McKinney | 564/488 |
| 5,310,905 | 5/1994 | Moran, Jr. | 540/540 |
| 5,359,061 | 10/1994 | Evans et al. | 540/540 |
| 5,359,062 | 10/1994 | Fuchs et al. | 540/540 |
| 5,360,905 | 11/1994 | Fuchs et al. | 540/540 |
| 5,441,607 | 8/1995 | Fuchs et al. | 203/49 |
| 5,455,346 | 10/1995 | Kopietz et al. | 540/540 |
| 5,457,197 | 10/1995 | Sifniades et al. | 540/540 |
| 5,468,900 | 11/1995 | Moran et al. | 562/590 |

FOREIGN PATENT DOCUMENTS

| | | | |
|---|---|---|---|
| 2143820 | 4/1994 | Canada | C07D 223/10 |
| 143502 | 11/1971 | Czech Rep. | C07D 201/12 |
| 0 522 235 | 6/1991 | European Pat. Off. | C07D 201/12 |
| 0568882 | 11/1993 | European Pat. Off. | C07D 201/12 |
| 608454 | 3/1994 | European Pat. Off. | C07D 201/12 |
| 0 676 394 | 3/1995 | European Pat. Off. | C07D 201/12 |
| 24 40 243 | 3/1976 | Germany | C07D 201/12 |
| WO 94/06763 | 3/1994 | WIPO | C07D 201/12 |

OTHER PUBLICATIONS

Serial No. 08/225,273, Sifniades et al., filed Apr. 8, 1994.
"The Re-equilibration of Polycaproamide", S. Smith, Journal of Polymer Science, vol. XXX, pp. 459–478 (1958).
"Regeneration of ε–Caprolactam From Wastes in the Manufacture of Polycaproamide Fibres and Yarns", Dmitrieva, et al., Fibre Chemistry, vol. 17, No. 4, Mar. 1986, pp. 229–241.
Fibre Chemistry, Dmitrieva et al., "Regeneration of E–Carprolactam from Wastes in the Manufacture of Polycaproamide Fibres and Yarn", vol. 17, No. 4, pp. 229–241.
Chemiefasern Textilindustrie, vol. 42, No. 6, 1992, p. 497.
Chem.–Ing.–Techn., R. Conrad, "Neue Chemische Verfahren", vol. 45, No. 24, 1973, pp. 1509–1524.

*Primary Examiner*—Robert T. Bond
*Attorney, Agent, or Firm*—Melanie L. Brown

[57] ABSTRACT

A process for recovering monomer from multi-component waste material that includes a hydrolyzable polymer, includes contacting the multi-component waste material with water and subjecting the resulting mixture to heat and pressure to form a liquid aqueous portion and a water insoluble portion. The liquid aqueous portion mainly includes depolymerization products of the hydrolyzable polymer, and the water insoluble portion mainly includes components other than the depolymerization products. This mixture is cooled and the liquid aqueous portion and the water insoluble portion are separated. Monomer that formed the hydrolyzable polymer is recovered from the liquid aqueous solution.

29 Claims, 2 Drawing Sheets

MONOMER RECOVERY FROM MULTI-COMPONENT MATERIALS

FIELD OF THE INVENTION

The present invention relates to an improved process for the recovery of monomers from multi-component, hydrolyzable polymeric waste materials, particularly caprolactam from waste materials that include nylon 6. The process is especially useful for recovering caprolactam from waste carpet materials including nylon 6 as a face fiber and non-nylon 6 components.

BACKGROUND OF THE INVENTION

Recovery of caprolactam from nylon 6 scrap, wherein the scrap is substantially free of non-nylon 6 materials, has been practiced for at least twenty years. In general, nylon 6 is depolymerized by heating at elevated temperatures, usually in the presence of a catalyst and/or steam. The caprolactam produced is removed as a vapor stream. An extensive review of the field has been given by L. A. Dmitrieva et al, Fibre Chemistry, Vol. 17, No. 4, March 1986, pp 229–241. Depolymerization of hydrolyzable polymers that are produced as scrap during the manufacture of fiber, chip, film or molded articles is also described in U.S. Pat. No. 4,605,762 to Mandoki. The process includes introducing the polymeric scrap into a hydrolyzer at a temperature of 200° to 300° C. and a pressure of at least 15 atmospheres, wherein high pressure steam is introduced into the lower portion of the hydrolyzer below the polymeric scrap. An aqueous solution of the products of the hydrolysis reaction is withdrawn from an upper portion of the hydrolyzer.

However, for multi-component mixtures or composites that contain nylon 6 as weld as other components, recovery of caprolactam is complicated by the presence of the other components. These other components and/or their decomposition products generated under conventional nylon 6 depolymerization conditions interfere with the isolation of caprolactam of adequate purity, thus necessitating expensive additional purification steps.

As an example of a product including nylon 6 as well as substantial amounts of other materials, carpet products made of a nylon 6 face fiber also include a backing (support) material which may include jute, polypropylene, latex (such as a styrene-butadiene rubber (SBR)) and a variety of inorganic materials such as calcium carbonate, clay or hydrated alumina fillers. Typically, the face fiber constitutes only 20–50% by weight of the carpet, with the rest of it consisting of the backing materials. In addition, the fiber may contain dyes, soil repellants, stabilizers and other compounds added during fiber and/or carpet manufacture. Waste carpet may also contain a host of other impurities, which will collectively be referred to herein as "dirt".

These non-nylon 6 components interfere with caprolactam recovery. For example, one of the most difficult problems is that alkaline components, such as the calcium carbonate filler, neutralize the acidic catalysts, such as phosphoric acid, that are conventionally used to promote nylon 6 depolymerization, thus requiring the use of increased amounts of catalyst. A further problem is that for waste material that includes substantial amounts of non-nylon 6 components, such as waste carpet material, the non-nylon 6 materials are difficult to process or handle.

It would be particularly beneficial if an inexpensive method could be developed for the recovery of caprolactam from multi-component composites or materials that include nylon 6, such as carpets, especially a method in which byproducts of non-nylon 6 components could be readily separated and handled.

SUMMARY OF THE INVENTION

The invention provides an improved process for recovering monomer from a multi-component polymeric waste material that includes at least one hydrolyzable polymeric component. The process comprises:

(a) subjecting a mixture of water and the multi-component polymeric waste material to heat and pressure to form a liquid aqueous solution which includes as a major constituent a mixture of depolymerization products of the hydrolyzable polymeric component and a water insoluble portion which includes as a major constituent a mixture of materials other than the depolymerization products;

(b) cooling the mixture resulting from step (a) and separating the liquid aqueous solution and the insoluble portion; and (c) recovering a monomer that formed the hydrolyzable polymeric component from the liquid aqueous solution.

The process is especially useful for recovering caprolactam from carpet material that includes nylon 6 and a significant amount of non-nylon components. The process facilitates practical separation of solids resulting from the non-nylon components. According to this embodiment, the invention provides a process for recovering caprolactam from carpet material that includes nylon 6 and non-nylon 6 components, wherein the process comprises:

(a) subjecting a mixture of water and the carpet material to heat and pressure to form a liquid aqueous solution which includes as a major constituent a mixture of nylon 6 depolymerization products and a water insoluble portion which includes as a major constituent a mixture of non-nylon 6 components;

(b) cooling the mixture resulting from step (a) and separating the liquid aqueous portion and the water insoluble portion; and (c) recovering caprolactam from the liquid aqueous solution.

DETAILED DESCRIPTION OF THE PREFERRED EMBODIMENTS

Figure 1:
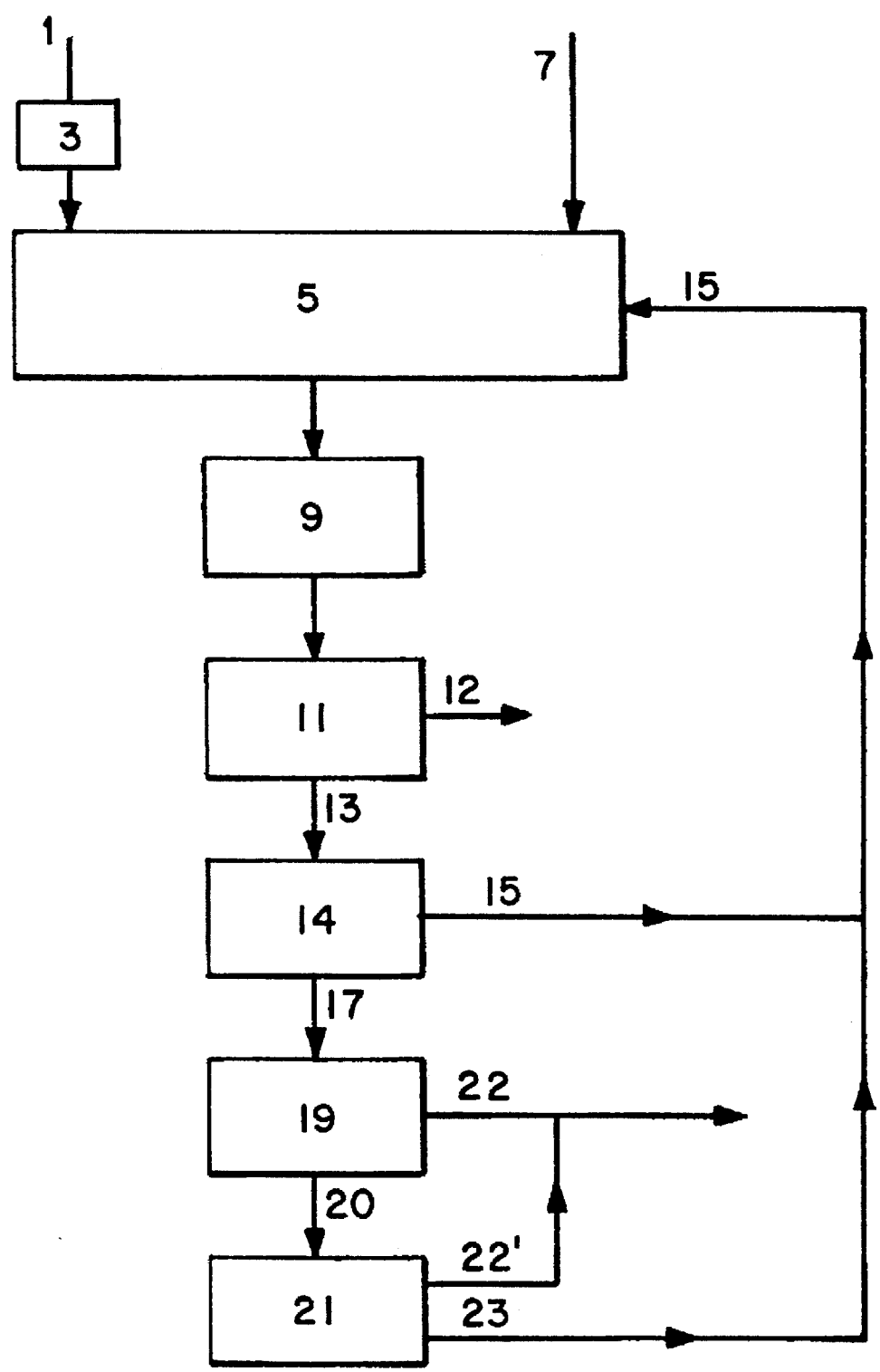
FIGS. 1 and 2 are schematic diagram of embodiments of the invention.

As used herein, "multi-component, polymeric waste material" denotes material or articles that include at least one hydrolyzable polymeric component and at least one other component which may be a non-hydrolyzable polymer, an inorganic or organic material, or other types of materials, and that have been, is intended to be, or otherwise would have been discarded by a consumer, manufacturer, distributor, retailer, installer and the like. The other components can constitute from about 5 to about 95, preferably about 20 to about 80 weight percent of the multi-component, polymeric waste material. "Multi-component, polymeric waste material" does not include waste material composed solely of scrap hydrolyzable polymeric and/or oligomeric material, such as material generated during the production of intermediate articles such as fiber, chip, film or molded articles which intermediate articles are then incorporated or transformed into end use multi-component products such as carpets and packaging. Examples of such scrap material are yarn waste, chip waste or extruder slag.

The hydrolyzable polymers with which this invention is particularly suitable include polyamide, especially nylon 6 and nylon 6,6, and polyester, especially polyethylene terephthalate. The recovered monomers are those from which the hydrolyzable polymer is formed. In the case of polyamide, the recovered monomers can be a dicarboxylic acid and an alkylene diamine or a lactum. With nylon 6 the recovered monomer is caprolactam and with nylon 66 the recovered monomers are adipic acid and hexamethylene diamine. In the case of polyester, the recovered monomers can be a dicarboxylic acid and a dihydric alcohol. With polyethylene terephthalate the recovered monomers are terephthalic acid and ethylene glycol.

One useful embodiment is the recovery of monomer from waste carpet material that includes a hydrolyzable polymer as the face fiber. Particularly useful is the recovery of caprolactam from waste carpet material that includes nylon 6 face fiber and non-nylon 6 components.

As used herein, "fiber" denotes an elongated body, the length dimension of which is much greater than the transverse dimensions of width and thickness. Accordingly, "fiber" includes, for example, monofilament, multifilament yarn (continuous or staple), ribbon, strip, staple and other forms of chopped, cut or discontinuous fiber, and the like having regular or irregular cross-sections. "Fiber" includes a plurality of any one of the above or a combination of the above.

As used herein, "carpet material" denotes carpet which has not been subjected to any mechanical separation (referred to herein as "whole carpet") and any mixture of carpet components that is a product of separation, mechanical or otherwise, of whole carpet (referred to herein as "beneficiated carpet"). "Waste carpet material" denotes carpet material that has been, is intended to be, or otherwise would have been discarded by a consumer, manufacturer, distributor, retailer, installer and the like.

An important benefit of the invention is that insoluble byproduct components, for example, the non-nylon components from the carpet backing and adhesive, form finely divided solid particles which can be easily separated from the liquid aqueous phase containing the desired monomer to be recovered. This benefit is especially important for waste carpet material considering that whole carpet may include less than the 50% by weight of nylon fiber.

A further advantage with respect to carpet is that the need for mechanical separation of the nylon 6 face fiber from the backing material and adhesive is avoided. Carpet without any prior treatment, including cleansing of waste carpet or removal of any treatment agents that have been applied to the face fiber such as stainblockers, soil repellants or stabilizers, may be used as the feedstock. If desired, however, the carpet may be mechanically reduced to strips or pieces of appropriate size to facilitate handling. Also, if desired, beneficiated carpet that includes nylon 6 face fiber that has been separated by mechanical means from part or most of the backing material and adhesive may be used as a feedstock, due to the flexibility of the process.

The process of the invention is described below in more detail, with particular reference to waste carpet material having nylon 6 face fiber as an example of the multi-component, polymeric waste material.

Initially, the waste carpet material and water are fed to a reactor or a series of reactors. The waste carpet material may be shredded prior to feeding to the reactor. The waste carpet material may added to the reactor, for example, using a polymer extruder or a process employing a continuous reactor, it may be advantageous to feed waste carpet material to the reactor via a pump suitable to maintain pressure in the reactor. As one example, dry shredded waste carpet material may be fed to the reactor via a piston pump. As another example, the waste carpet material may be heated so as to at least partially melt the material, and then fed to the reactor via a gear pump.

Water is added to the reactor to form a mixture of water and the multi-component polymeric waste material, and the mixture is subjected to heat and pressure to form a liquid aqueous solution which includes as a major constituent a mixture of depolymerization products of the hydrolyzable polymeric component and a water insoluble portion which includes as a major constituent a mixture of materials other than the depolymerization products. The water may be supplied as liquid water, superheated steam or as a mixture of liquid water and steam. In the last two instances a steam superheater may be used to obtain a desired temperature and pressure. In any case, most steam entering the reactor condenses into liquid water. The reactor pressure is near the vapor pressure of water at the operating temperature.

In the reactor, the mixture of water and the carpet material is subjected to heat and pressure to form a liquid aqueous solution which includes as a major constituent a mixture of nylon 6 depolymerization products and a water insoluble portion which includes as a major constituent a mixture of non-nylon 6 components. For a batch process, a stirred autoclave reactor may be employed. For a continuous process, a stirred tank reactor may be used, preferably at least three stirred tank reactors connected in series.

The amount of water used relative to the waste material should be sufficient to dissolve a substantial portion of the hydrolyzable polymeric component and depolymerization products and extract them from the other components present in the waste material. The amount of water will depend on the desired hydrolyzable polymer and depolymerization product recovery, the hydrolyzable polymer content of the carpet, the temperature, and the mode of extraction. Generally, the higher the desired recovery, the higher the required amount of water and the higher the temperature of the reaction. For the described embodiment employing waste nylon 6 carpet material, the preferred amount of water is about 0.5 to about 7, especially about 2 to about 7, and more preferably about 4 to about 6, parts of water per part nylon 6 present in the carpet.

The reaction temperature during this stage should be greater than the melting point of the hydrolyzable polymeric component. Preferably, the temperature should be at least about 5° C., more preferably at least about 10° C., above the melting point. In the described embodiment where the hydrolyzable polymeric component is nylon 6, the reaction temperature during this stage should be at least about 240° C. At lower temperatures reaction of nylon 6 with water is very slow. Higher temperatures increase the rate of reaction and minimize the amount of nylon 6 depolymerization products that remain in the water insoluble phase, but also require higher pressure because of the increased vapor pressure of water. A temperature range of about 240° to about 375° C. is appropriate for this stage, with a preferred range of about 250° to about 350° C., most preferably about 285° to about 305° C. The reaction pressure during this stage is dependent on the reaction temperature, and is approximately equal to the vapor pressure of water at the temperature of the reaction, which is in the range of about 465 to about 2700 psi (about 3200 to about 18,600 kPa).

This stage of the process accomplishes two main tasks: the dissolution of nylon 6 in water and the partial depolymerization of nylon 6. The nylon 6 dissolution and the nylon 6 depolymerization may occur simultaneously. Depolymerization is manifested by an increase in the concentration of amine and carboxylic end groups and by formation of caprolactam. The caprolactam being produced appears to facilitate the dissolution of additional nylon 6 and its oligomers. Furthermore, it is believed that the high concentration of end groups facilitates depolymerization in the process. Moreover, as the degree of depolymerization increases the solubility of the nylon 6 hydrolyzate in water increases and the viscosity of the liquid aqueous solution decreases. Because of the decreased viscosity, the liquid aqueous solution and the water insoluble portion tend to achieve a more distinct separation.

At least about 60, preferably at least about 80, and most preferably at least about 90, weight % of the nylon 6 depolymerization products formed during this stage, based on the weight of the amount of nylon 6 depolymerization products theoretically available in the carpet feedstock, should be dissolved in the aqueous solution formed in this stage. Viewed another way, at least about 80, preferably at least about 90, and most preferably at least about 99, weight % of the nylon 6 theoretically available in the carpet feedstock is extracted. The nylon 6 depolymerization products form the major constituent of the liquid aqueous solution. By "major constituent" it is meant that the mixture of nylon 6 depolymerization products is the largest constituent or component of the liquid aqueous solution by weight, excluding water. Preferably, the resulting concentration of nylon 6 depolymerization products in the liquid aqueous solution should be at least about 5, more preferably at least about 15, and most preferably at least about 20, weight %.

The water insoluble portion resulting from this stage should include at least about 90, preferably about 95, and most preferably about 99, weight % of the non-nylon 6 components, based on the weight of the non-nylon 6 components in the carpet feedstock. In particular, if the waste carpet material includes calcium carbonate, polypropylene and SBR latex, the water insoluble portion should include about 99.8 to about 96.5 weight % of the calcium, and about 90 to about 99 weight % the non-nylon 6 components other than calcium carbonate. The non-nylon 6 components form the major constituent of the water insoluble portion. By "major constituent" it is meant that the mixture of non-nylon 6 components is the largest constituent or component of the water insoluble portion by weight, excluding absorbed or entrained water. Preferably, the resulting amount of non-nylon 6 components in the water insoluble portion should be at least 90, more preferably at least 95, weight %, based on the weight of the water insoluble portion exclusive of absorbed or entrained water. Typically, the maximum amount of non-nylon 6 components in the water insoluble portion can reach up to about 99 weight %, based on the weight of the water insoluble portion exclusive of absorbed or entrained water.

It is important that the reaction mixture in this stage include a liquid aqueous phase into which the depolymerization products can dissolve. Small amounts of nylon 6 depolymerization products, however, are lost in the water insoluble portion by virtue of reduced solubility in the aqueous solution, increased solubility, absorption, adsorption, or mechanical entrainment in the water insoluble phase, or other physical effects. Generally, the higher molecular weight fraction of said products tends to remain in the water insoluble portion. The loss can be minimized by operating at higher temperatures, using larger amounts of water, and increasing the contact time between the carpet material and water, as can be readily determined by one skilled in the art.

The next main stage of the process of the invention involves separation of the liquid aqueous phase and the water insoluble phase formed by the preceding stage. It is a critical aspect of the invention that the separation occurs at a lower temperature than exists in the reactor. Preferably, cooling is provided so that separation occurs at a substantially reduced temperature from that of this stage. It has been found that by reducing temperature below that of this stage, solidification of the insoluble components is allowed. Surprisingly, it has been found that separation at the reduced temperature provides the insoluble components in the form of finely divided solid particles which settle readily, can be more easily separated from the liquid aqueous phase, and can be more easily removed from the reactor.

More specifically, this stage of the process of the invention involves separation of the liquid aqueous phase and the water insoluble phase formed by the first stage. As mentioned, separation is conducted at a lower temperature than the first stage. Preferably, the second stage involves a cooling step between the first stage and this initial separation. In this cooling step, the reaction products are cooled to below about 150° C., more preferably to below about 100° C., most preferably to a temperature in the range of about 70° to about 95° C., thereby reducing the pressure and solidifying the water insoluble portion. If the reaction is conducted in a batch reactor the cooling can be accomplished using indirect cooling provided by cooling coils or evaporative cooling by venting the reactor to atmospheric pressure through a condenser. If the reaction is conducted in a continuous reactor, cooling can be accomplished by flashing the reactor contents to atmospheric pressure in a flash tank or by passing the mixture through a water cooled heat exchanger. The cooling coils or heat exchangers can optionally be used as boilers to produce steam for process heating or evaporation.

It was unexpectedly found that the water insoluble components in the carpet (which can include, e.g., polypropylene, calcium carbonate and styrenebutadiene rubber) form a plurality of finely divided solid particles which are readily separated from the water soluble hydrolysis products by well known mechanical means such as centrifuging, or filtration. Without the reduced temperature, in the case of whole carpet feedstock, the insoluble matter after the first stage tends to form a rubbery mass. In contrast, for the present invention, the insoluble portion, formed mainly of the finely divided solids, can be easily removed from the reactor and readily separated from the liquid aqueous portion by conventional means. The solids can optionally be combusted in a separate step to provide energy for process heating and evaporation.

The next main stage of the process involves recovery of the desired monomer that formed the hydrolyzable polymeric component from the liquid aqueous medium. For the described embodiment, the desired monomer to be recovered is caprolactam.

Generally, it is preferred that the recovery includes a step of removing a substantial amount of the water, e.g., at least about 75, more preferably at least about 95 weight %, and including even over 99 weight %, from the liquid aqueous portion to form an enriched stream of caprolactam and the other depolymerization products, followed by separating caprolactam from the other depolymerization products.

The water removal can be accomplished by various means, such as a distillation process. As one example, the liquid aqueous portion can be charged to a water flasher, followed by a distillation column. Preferably, both the flasher and the distillation column are operated at a temperature of less than about 110° C., preferably of less than 100° C., most preferably at a temperature below about 90° C. The overheads from the distillation process (consisting substantially of water vapor) may be recycled to the reactor.

Following the water removal step, the enriched stream including caprolactam and other depolymerization products can then be subjected to any of various methods known generally in the art for separating caprolactam from other nylon depolymerization products, such as a second distillation process. As one example, a lactam flash tank can be employed, followed with a thin film evaporator to recover crude caprolactam. Preferably, these processes are conducted at a temperature in the range of from about 100° to about 150° C., and more preferably in the range of from about 120° to about 135° C. At the lower temperatures, repolymerization of the caprolactam and oligomers to form higher molecular weight compounds is inhibited.

Optionally, the resultant stream enriched with depolymerization products may be charged to a flash tank and contacted with superheated steam, according to processes known in the art. As an example, U.S. Pat. No. 4,764,607, incorporated herein by reference, discloses a suitable apparatus for mixing a liquid mixture containing caprolactam with superheated steam. In some cases, this embodiment may be useful for providing a more efficient separation of caprolactam from oligomers. The caprolactam is vaporized with the superheated steam. Since temperatures in the tank may be significantly above the temperature at which repolymerization of caprolactam would generally occur, it is important that a low residence time, i.e., below 1 second, is maintained in the flasher. The caprolactam exiting this flasher with the steam can be charged to a partial condenser or to a column to condense the caprolactam. The bottoms from the flash tank, composed primarily of oligomers, can be recycled to the reactor.

The purity of the caprolactam recovered at this point in the process should range from about 96 to 99 weight %. The 1 to 4 weight % of impurities in the crude caprolactam includes oligomers. If beneficiated carpet is used as the feedstock, the purity will tend to be higher. If there is a significant amount of dirt on the carpet, the purity will tend to be lower.

Following the caprolactam recovery, caprolactam of polymerization grade may be obtained by further purification in downstream operations using known purification processes known to those of ordinary skill in the art, such as crystallization, vacuum distillation after treatment with acid or alkali, ion exchange, permanganate treatment, and hydrogenation. The residue, which contains caprolactam, cyclic oligomers, and linear oligomers, can advantageously be recycled to the initial reactor, and a portion of the recycle stream can be removed to purge impurities.

Figure 2:
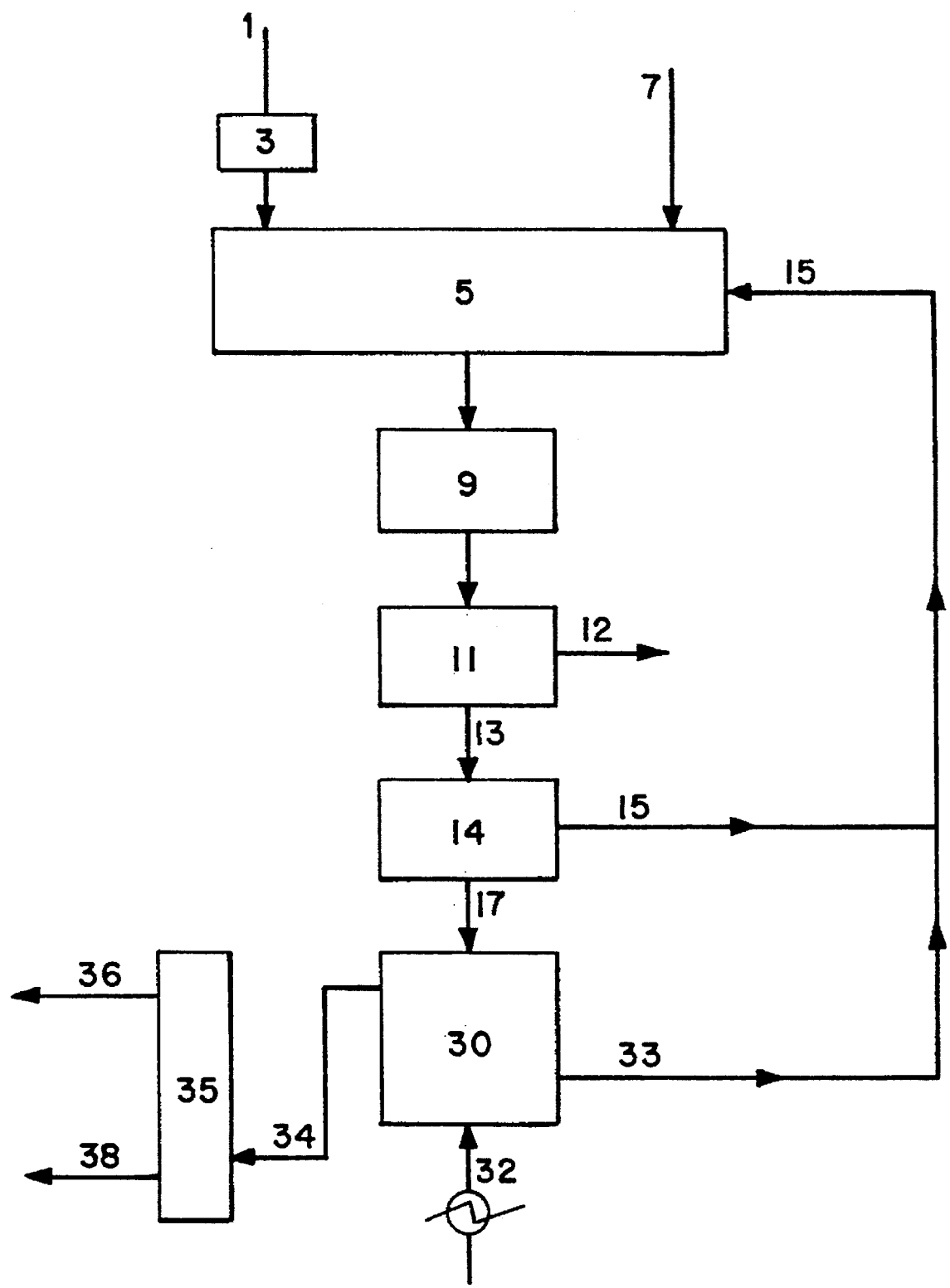

FIGS. 1 and 2 are schematic diagrams of representative embodiments of the process of the invention.

A carpet with face fiber of nylon 6, backing of polypropylene and calcium carbonate-filled SBR latex is shredded into strips and fed at 1 to reactor 5. For a continuous reactor, the carpet strips are fed via extruder or pump 3 in a manner to maintain pressure in reactor 5. Water is charged to the reactor at 7 (and via recycle stream 15) where the mixture is reacted at a temperature of between about 250° and about 375° C., at a reaction pressure of between about 465 to about 2700 psi (about 3200 to about 18,400 kPa), for from about 15 minutes to about 1 hour. For a batch process, reactor 5 may be a stirred autoclave reactor. For a continuous process, a stirred tank reactor may be used, preferably at least three stirred tank reactors connected in series. The depolymerized nylon 6 and water insoluble carpet components are then cooled at 9, by either indirect heat exchange or flash cooling, most preferably to a temperature in the range of from about 70° to about 95° C. The water insoluble components are separated from the water soluble depolymerization products at 11, via a process such as centrifuging or filtration. The water insoluble components exiting the system at 12 have the form of finely divided solids, and may be combusted to provide energy to the system. A substantial amount of water, preferably at least 75 weight %, is removed from stream 13 (that includes the water soluble depolymerization products) at 14 via a distillation process wherein the temperature is preferably maintained in the range of from about 50° to about 135° C. The water can be recycled via stream 15 to the reactor. Crude caprolactam is then recovered from the other depolymerization products in stream 17.

As shown in FIG. 1, the separation of caprolactam from other depolymerization products in stream 17 can be conducted in a distillation process. Stream 17 is charged to flasher 19, wherein crude caprolactam 22 can optionally be purified in downstream operations. The bottoms 20 of flasher 19 will be composed primarily of oligomers, but any additional caprolactam in stream 20 can be collected in thin film evaporator 21 and exit as stream 22'. Preferably, flasher 19, as well as evaporator 21, are maintained within the more preferred range of from about 120° to about 135° C. to inhibit repolymerization of caprolactam. Residue 23, which contains cyclic oligomers and linear oligomers, and minor amounts of caprolactam, can advantageously be recycled to the initial reactor. A portion of the recycle stream can be removed to purge impurities (not shown).

As shown in FIG. 2, stream 17 is charged to flash tank 30 where it is contacted with superheated steam 32. Residence time of the depolymerization products is maintained below 1 second since temperature in tank 30 may exceed 200° C. The overhead 34 from flash tank 30 is charged to partial condenser or column 35 where crude caprolactam 38 is recovered, which can optionally be purified in downstream operations. Residue 33 can be recycled to reactor 5, and a portion of this recycle stream can be removed to purge impurities (not shown). Water 36 may be disposed.

The following example illustrates various preferred embodiments. The specific techniques, conditions, materials, proportions and reported data set forth to illustrate the principles of the invention are exemplary and should not be construed as limiting the scope of the invention. Unless otherwise stated, all parts and percentages are by weight.

EXAMPLE 1

An embodiment of the invention involving a continuous process follows.

Twenty thousand pounds per hour of waste carpet manufactured from nylon 6, containing about 50 wt. % nylon 6, is shredded into strips, approximately 3 in×5 in and charged to extruder 3. The extruder melts the carpet and discharges into the reactor which is comprised of three vessels in series. The vessels are 10000 gallon agitated, jacketed tanks and are heated with a heat transfer fluid. The heat transfer fluid maintains the temperature in the reactor at approximately 295° C. and the pressure at approximately 1150 psi, and provides additional heat to complete the reaction over the heat supplied by the extruder and hot water. Fifty six thousand pounds per hour of hot water is added to the reactor through a heater which heats the water to 295° C. Four thousand one hundred pounds per hour of residue from the film evaporator (described below), which contains oligomers, is mixed with recycle water in a mix tank, and is added to reactor 5.

The reaction products from the reactor are discharged through a pressure reducing valve into a vessel. The vessel is a five thousand gallon jacketed flash tank with an agitator and a condenser; the condenser condenses steam produced during flashing and returns the condensate to the vessel. The energy contained in the steam can be used to preheat the water added to the reactor, or can be recovered in another manner using methods familiar to those skilled in the art. Cooling water is supplied to the jacket of the vessel to maintain the temperature at about 90° C.

Eighty thousand pounds per hour of slurry from the flash tank is pumped to a centrifuge where approximately ten thousand pounds per hour of solids, containing backing materials used in carpet manufacture such as polypropylene and calcium carbonate, are removed. The centrifuge liquor is filtered to remove residual solids and pumped to an evaporator in which fifty six thousand pounds per hour of water is removed and recycled to the reactor. A portion of the water, about five thousand pounds per hour, is purged to remove accumulated impurities. The purged water is replaced by purified water. The evaporator is operated at about 95° C., 450 mm Hg to minimize polymerization of caprolactam. Approximately fourteen thousand one hundred pounds per hour of concentrated nylon 6 values, containing about 100 pounds per hour of water, ten thousand one hundred pounds per hour of caprolactam, two thousand two hundred pounds per hour of oligomers, and one thousand seven hundred pounds per hour of accumulated impurities, is withdrawn from the evaporator and pumped into a caprolactam flasher.

The caprolactam flasher is comprised of a flash tank, heater, recycle pump and condenser. The flasher is operated at a pressure of approximately six mm Hg and a temperature of about 125° C. to minimize polymerization of caprolactam. Approximately eight thousand pounds per hour of caprolactam is distilled overhead and condensed. The residue from the flasher is pumped to a wiped film evaporator and condenser to recover additional caprolactam values. The wiped film evaporator is operated at about 5 mm Hg absolute pressure and 135° C. to minimize polymerization of caprolactam. An additional one thousand one hundred pounds per hour of caprolactam is condensed and combined with the caprolactam originally obtained from the caprolactam flasher; the crude caprolactam may be purified to produce fiber grade caprolactam using methods known in the art. Approximately four thousand nine hundred pounds per hour of residue is drained from the wiped film evaporator 21, of which approximately eight hundred pounds per hour is purged and the remaining four thousand one hundred pounds per hour is combined with condensate from the initial evaporator and recycled to the reactor.

EXAMPLE 2

A carpet having nylon 6 face fiber and backing of polypropylene and calcium carbonate-filled SBR latex contained 46% nylon 6, 7% polypropylene, and 48% $CaCO_3$/SBR. 980.0 g of water was charged to a 2.0 liter stirred autoclave reactor and heated to 240° C. A polymer extruder was preheated to 260° C., and 343.0 g of waste carpet strips were charged to the extruder feed hopper and fed into the reactor.

The reactor was heated to about 310° C. and held at that temperature for about one hour. The reactor was thereafter rapidly cooled to about 90° C. using cooling water. 1291 g of material were recovered (97.6%). The granular solids were separated from the aqueous phase by filtering. The aqueous phase contained 11.3 weight % caprolactam which corresponds to about 79.1% recovery of the nylon 6 as caprolactam. The water was distilled from the depolymerization products using a rotary vacuum evaporator. The temperature was maintained at less than about 80° C. by maintaining pressures of 6 psi or less. The residue was transferred to a round bottom flask fitted with a heating mantle and condenser. The caprolactam was distilled from the other depolymerization products using a vacuum of 5 mm Hg. Distillation was terminated when the distilling temperature reached about 135° C. About 90% of the caprolactam was recovered. The crude caprolactam contained less than 1000 ppm impurities.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for recovering monomer from a multi-component polymeric waste material that includes at least one hydrolyzable polymeric component, comprising:

(a) subjecting a mixture of water and the multi-component polymeric waste material to heat and pressure to form a liquid aqueous solution which includes as a major constituent a mixture of depolymerization products of the hydrolyzable polymeric component and a water insoluble portion which includes as a major constituent a mixture of materials other than the depolymerization products;

(b) cooling the mixture resulting from step (a) at a temperature at which the water insoluble portion forms a plurality of finely divided solid particles;

(c) separating the liquid aqueous solution and the finely divided solid particles; and (d) recovering a monomer that formed the hydrolyzable polymeric component from the liquid aqueous solution.

2. The process according the claim 1, wherein the liquid aqueous solution is cooled to below about 150° C.

3. The process according to claim 2, wherein the liquid aqueous solution is cooled to a temperature in the range of from about 70° to about 100° C.

4. The process according to claim 1, wherein step (d) includes removing water from the liquid aqueous solution, followed by separating the monomer from other depolymerization products of the hydrolyzable polymeric component.

5. The process according to claim 4, wherein at least about 75% of water, based on total weight of water in the liquid aqueous solution, is removed prior to the separation of the monomer.

6. The process according to claim 4, wherein water is removed by distillation or evaporation, prior to the separation of the monomer.

7. The process according to claim 4, wherein the monomer is separated from the other depolymerization products by distillation.

8. The process according to claim 7, wherein the distillation is conducted at a temperature in the range of from about 100° to about 150° C.

9. The process according to claim 8, wherein the distillation is conducted at a temperature below about 135° C.

10. The process according to claim 4, wherein separation of caprolactam from the other depolymerization products includes contacting a stream including the caprolactam and other depolymerization products with superheated steam, followed by condensation.

11. The process according to claim 1, wherein the hydrolyzable polymeric component comprises a polyamide and the monomer comprises a lactam.

12. The process according to claim 1, wherein the hydrolyzable polymeric component comprises a polyamide and the monomer comprises at least one of the group consisting of a dicarboxylic acid and an alkylene diamine.

13. A process for recovering caprolactam from carpet material that includes nylon 6 and non-nylon 6 components, comprising:
  (a) subjecting a mixture of water and the carpet material to heat and pressure to form a liquid aqueous solution which includes as a major constituent a mixture of nylon 6 depolymerization products and a water insoluble portion which includes as a major constituent a mixture of non-nylon 6 components;
  (b) cooling the mixture resulting from step (a) at a temperature at which the water insoluble portion forms a plurality of finely divided solid particles;
  (c) separating the liquid aqueous portion and the finely divided solid particles; and (d) recovering caprolactam from the liquid aqueous solution.

14. The process according to claim 13, wherein the liquid aqueous solution is cooled to below about 150° C.

15. The process according to claim 14, wherein the liquid aqueous solution is cooled to a temperature in the range of from about 70° to about 100° C.

16. The process according to claim 13, wherein step (d) includes removing water from the liquid aqueous solution, followed by separating caprolactam from other depolymerization components.

17. The process according to claim 16, wherein at least about 75% of water, based on total weight of water in the liquid aqueous solution, is removed from the liquid aqueous solution prior to the separation of caprolactam.

18. The process according to claim 17, wherein the water is removed by distillation or evaporation, prior to the separation of caprolactam.

19. The process according to claim 16, wherein caprolactam is separated from the other depolymerization products by distillation.

20. The process according to claim 19, wherein the distillation is conducted at a temperature in the range of from about 100° to about 150° C.

21. The process according to claim 20, wherein the distillation is conducted at a temperature below about 135° C.

22. The process according to claim 16, wherein separation of caprolactam from the other depolymerization products includes contacting a stream including the caprolactam and other depolymerization products with superheated steam, followed by condensation.

23. The process according to claim 13, wherein the amount of water contacted with the carpet material is from about 0.5 to 7 parts of water per one part nylon 6 present in the carpet material, based on weight.

24. The process according to claim 13, wherein step (a) comprises subjecting the carpet and water mixture to sufficient heat and pressure to initiate depolymerization of nylon 6 and extract the resulting nylon 6 depolymerization products from the carpet material into the liquid aqueous portion.

25. The process according to claim 13, further comprising purifying crude caprolactam recovered from the liquid aqueous solution.

26. The process according to claim 13, further comprising recycling a residue from step (c) to mix with the carpet material feed in step (a).

27. A process according to claim 13, wherein the non-nylon 6 components include at least one material selected from the group consisting of jute, polypropylene, latex, calcium carbonate, clay and hydrated alumina.

28. A process for recovering caprolactam from a carpet material that includes nylon 6 and non-nylon 6 components, comprising:
  (a) introducing the carpet material and water into a reactor;
  (b) subjecting the resulting mixture to heat and pressure to form a liquid aqueous portion which includes a s a major constituent a mixture of nylon 6 depolymerization products and a water insoluble portion which includes as a major constituent a mixture of non-nylon 6 components;
  (c) cooling the mixture resulting from step (b) at a temperature at which the water insoluble portion forms a plurality of finely divided solid particles; and
  (d) separating the liquid aqueous solution and the finely divided solid particles;
  (e) removing at least 75% water from the liquid aqueous solution; and
  (f) separating caprolactam from other depolymerization products.

29. The process according to claim 28, further comprising purifying the caprolactam separated from the other components.

* * * * *